(12) United States Patent
Rochford et al.

(10) Patent No.: US 10,466,176 B2
(45) Date of Patent: Nov. 5, 2019

(54) SYSTEM AND METHOD FOR DETECTING CONTAMINANTS ON A CIRCUIT

(71) Applicant: BAE SYSTEMS INFORMATION AND ELECTRONIC SYSTEMS INTEGRATION INC., Nashua, NH (US)

(72) Inventors: Richard Rochford, Litchfield, NH (US); Tristan J. Baldwin, New Boston, NH (US); Edward L. Brabant, Jr., Dracut, MA (US); Charles H. Mazel, Bedford, MA (US); Michael J. Meade, Nashua, NH (US)

(73) Assignee: BAE Systems Information and Electronic Systems Integration Inc., Nashua, NH (US)

( * ) Notice: Subject to any disclaimer, the term of this patent is extended or adjusted under 35 U.S.C. 154(b) by 0 days.

(21) Appl. No.: 15/583,480

(22) Filed: May 1, 2017

(65) Prior Publication Data

US 2018/0313757 A1    Nov. 1, 2018

(51) Int. Cl.
*G01N 21/64* (2006.01)
*G02B 21/16* (2006.01)
(Continued)

(52) U.S. Cl.
CPC ..... *G01N 21/6447* (2013.01); *G01N 21/8803* (2013.01); *G01N 21/8806* (2013.01);
(Continued)

(58) Field of Classification Search
CPC ........... G01N 21/6447; G01N 21/8803; G01N 21/8806; G01N 21/8851; G01N 21/94; G01N 15/1475; G02B 21/0016; G02B 21/16; H01L 21/02057; H01L 21/67288; H01L 22/20; H04N 5/225; H04N 5/2256; G06F 19/00; C12Q 1/04; C12M 1/34
See application file for complete search history.

(56) References Cited

U.S. PATENT DOCUMENTS 5,479,252 A * 12/1995 Worster ............ G01N 21/9501
250/559.42
6,005,964 A * 12/1999 Reid ................... G01N 15/1475
378/42

(Continued)

OTHER PUBLICATIONS

International Search Report, PCT/US2018/030134, dated Jul. 9, 2018, 15 pages.

(Continued)

*Primary Examiner* — Jamil Ahmed
(74) *Attorney, Agent, or Firm* — Sand, Sebolt & Wernow LPA; Scott J. Asmus

(57) ABSTRACT

The present disclosure relates to a system and method utilizing a light source coupled with a viewing device to detect contaminant(s) on an electronic circuit board. This fluorescence microscopy apparatus can be easily integrated into a bench top stereoscope or microscope and does not require the use of expensive and destructive analytical techniques. Typically, blue light is used in conjunction with a filter to detect contamination from cured epoxy resins and many other contaminants on gold bond pads, wires, pads, or other electrically conductive elements on the electronic circuit.

16 Claims, 8 Drawing Sheets

(51) Int. Cl.
*G01N 21/88* (2006.01)
*G02B 21/00* (2006.01)
*H01L 21/67* (2006.01)
*H01L 21/66* (2006.01)
*H01L 21/02* (2006.01)
*G01N 21/94* (2006.01)
*G02B 21/24* (2006.01)
*G02B 5/20* (2006.01)
*G01N 21/956* (2006.01)

(52) U.S. Cl.
CPC ......... *G01N 21/94* (2013.01); *G02B 21/0016* (2013.01); *G02B 21/16* (2013.01); *G02B 21/24* (2013.01); *G01N 2021/95638* (2013.01); *G02B 5/208* (2013.01)

(56) References Cited

U.S. PATENT DOCUMENTS

| | | | |
|---|---|---|---|
| 6,377,345 | B1 | 4/2002 | Powell |
| 2006/0008866 | A1* | 1/2006 | Flick .................. G01N 21/6447 435/34 |
| 2008/0027665 | A1* | 1/2008 | Takahashi .......... G01N 21/8851 702/70 |
| 2009/0057611 | A1* | 3/2009 | Hirosaki ............ C09K 11/0883 252/301.4 R |
| 2014/0152801 | A1 | 6/2014 | Fine et al. |
| 2016/0350909 | A1* | 12/2016 | Chu ..................... H04N 5/2256 |

OTHER PUBLICATIONS

Heltzel, Stan, "Latent short circuit failure in high-rel PCBs caused by lack of cleanliness of PCB processes and base materials," European Space Agency, Components Technology and Space Materials Division, Noordwijk, Netherlands, Aug. 2015, pp. 1-8.

Sita Fluoscan 3D, https://www.sita-process.com/products/fluorescence-measuring-and-testing-devices/sita-fluoscan-3d/, Accessed May 1, 2017.

Light Head Hanger System for the Stereo Microscope Fluorescence Adapter, https://www.nightsea.com/products/sfa-light-head-hanger/, Accessed May 1, 2017.

Light Head Hanger system for the Stereo Microscope Fluorescence Adapter, https://web.archive.org/web/20160429050845/https://www.nightsea.com/products/sfa-light-head-hanger/, Accessed May 1, 2017.

Tristan Baldwin, Visual Identification of Organic Residue on Microelectronic Components via In-Process Visible Light Fluorescence, IMAPS New England Symposium and Expo, May 2017, 1 page, United States.

Tristan Baldwin, Blue Light (460nm) Fluorescence for the Detection of Organic Contamination in Microelectronic Assemblies, IMAPS New England Symposium and Expo, May 2017, 25 pages, United States.

Nightsea, Stereo Microscope Fluorescence Adapter, Published Jan. 19, 2014, retrieved from https://www.nightsea.com/products/stereomicroscope-fluorescence-adapter/ on Aug. 8, 2018, United Stated.

Keyence, VHX-6000 Digital Microscope, retrieved from https://www.keyence.com/ss/products/microscope/vhx-6000/, Aug. 8, 2018, United States.

Sita Process Solutions, FluoScan 3D, retrieved from https://www.sita-process.com/products/fluorescence-measuring-and-testing-devices/sita-fluoscan-3d/, Aug. 15, 2018, United States.

Nightsea, Light Head Hanger System for the Stereo Microscope Fluorescence Adapter, Published Jan. 19, 2014, retrieved from https://www.nightsea.com/products/sfa-light-head-hanger/ on Aug. 15, 2018, United Stated.

* cited by examiner

SYSTEM AND METHOD FOR DETECTING CONTAMINANTS ON A CIRCUIT

BACKGROUND

Technical Field

The present disclosure relates generally to a method and system for detecting contaminants on a microelectronic circuit. More particularly, the present disclosure relates to a system and method of detecting contaminants on microelectronic circuits utilizing light in a first wavelength range that generates fluorescent feedback from a contaminant particle in a second wavelength range. More particularly, the present disclosure relates to the use of blue light to generate a fluorescent feedback from a contaminant particle coupled with a filter in a microscope or other viewing device that filters out the background blue light so as to only reveal the fluorescent feedback in the microscope or other viewing device.

Background Information

Microelectronic circuits or integrated circuits are small electrical devices configured to carry electrical current in the transmission of signals between electrical devices. The transmission of signals moving along the microelectronic circuits or integrated circuits is most efficient when the physical wiring is free from contaminants or other particles or residue that hinder the conduction of electricity through the wires. Some exemplary contaminants are the epoxy resins used to adhere the wires to the substrate of the microelectronic circuit. Furthermore, some of the epoxy resins used to bond the wires to the substrate are organically based.

Detection of organic epoxy residues contaminated on gold wires or gold ribbon bonded to the surface of the microelectronic circuit board using a white light microscopic device is difficult. Thin, electrically insulating resin layers (contamination) are often not easily detectable or invisible to persons using a white light microscope. While fluorescence is commonly used to observe conformal coatings, such visual techniques have previously proven ineffective for the detection of organic epoxy resins in microelectronic hardware. When epoxy resins contaminate a circuit/chip or a wire assembly, it is difficult to detect the resins using low cost in-process techniques. However, detection of these contaminants on wiring or ribbon bondings would yield improvements in circuit reliability and efficiency.

The concept of utilizing fluorescent response typically utilizes ultraviolet (UV) light (which is dangerous to humans) in order to illicit a fluorescent response from the particle that has been excited from the incoming light. Typically, it is important to get a high degree of fluorescent efficiency. Fluorescent efficiency can be accomplished by exciting a particle with a low excitation power then viewing the fluorescent response in a high power microscope. Alternatively, it is possible to excite a particle with a highly powerful excitation wavelength and view the fluorescent response with a simple viewing device or the human eye. In each scenario, a photon from the excitation wavelength hits an electron on the particle and the electron on the particle is promoted to an excited higher level of energy. Then, when the excited particle drops down from the excited state to an unexcited state, there is a longer wavelength light that is produced. Thus, for example, if an initial excitation wavelength in the UV band is approximately 100 nm, then the resultant fluorescent feedback band would be greater than 100 nm and could be about 200 nm.

SUMMARY

Therefore, there is need for a new apparatus or system to detect organic resin contaminants on a microelectronic circuit board, which is nonhazardous to an operator and can be built in low cost.

In one example, a fluorescence viewing capability can be integrated into an existing bench top stereoscope so that the stereoscope does not require expensive or destructive analytical techniques, such as IR spectroscopy or X-ray photoelectron spectroscopy (XPS). Similarly, this apparatus or system may be adapted for use on modules of any size. Unlike UV fluorescence techniques, no hazardous wavelengths of light are used.

In one example, a system for detecting contaminants on an electronic circuit may include a viewing device adapted to view an electronic circuit having an electrically conductive element bonded to a substrate; a first light source emitting light at a first wavelength towards the electronic circuit adapted to excite particles on the electronic circuit at a fluorescent feedback second wavelength generated in response to particle excitation from the first light source, wherein the second wavelength is greater than the first wavelength; and a filter in operative communication with the viewing device having a selected filter wavelength configured to allow light to pass that is greater than the first wavelength.

In one example a system for detecting contaminants on an electronic circuit may include: a viewing device adapted to view an electronic circuit having an electrically conductive element bonded to a substrate; a first light source emitting light at a first wavelength towards the electronic circuit adapted to excite particles on the electronic circuit at a fluorescent feedback second wavelength generated in response to particle excitation from the first light source, wherein the second wavelength is greater than the first wavelength; and a filter in operative communication with the viewing device having a selected filter wavelength configured to preclude passage of light beyond the selected filter wavelength, wherein the selective filter wavelength is greater than the first wavelength and less than the second wavelength (stated otherwise, the filter filters lights bands/wavelengths shorter than the selected filter wavelength). This example may further be implemented in a computer, such that the filter is a digital filtering logic in operative communication with a computer and the viewing device, and the system further comprising: at least one non-transitory computer readable storage medium in having instructions encoded thereon that, when executed by one or more processors, result in the following operations for detecting the contaminant on the electronic circuit, the operations configured to: (a) emit light from the first light source at the first wavelength toward the electronic circuit; (b) effect the excitation of particles on the electronic circuit with the light having the first wavelength, wherein the particles generate the fluorescent feedback second wavelength in response to the excitation and the second wavelength is greater than the first wavelength; (c) view the fluorescent feedback second wavelength with the viewing device; and (d) determine whether the contaminant is present on electrically conductive element based on viewing the fluorescent feedback second wavelength and execution of the digital filtering logic.

In one example, an aspect of the present disclosure may provide a system for detecting contaminants on an electronic circuit comprising: an electronic circuit having electrically conductive element bonded to a substrate; a viewing device adapted to view the electronic circuit; a first light source emitting light at a first wavelength towards the electronic circuit configured to excite particles on the electronic circuit; a fluorescent feedback second wavelength of the excited particles generated in response to particle excitation from the first light source, wherein the second wavelength is greater than the first wavelength; and a filter in operative communication with the viewing device having a selected filter wavelength configured to preclude passage of light beyond the selected filter wavelength, wherein the selective filter wavelength is greater than the first wavelength and less than the second wavelength. This example or another example may further provide wherein the excited particles generated in response to particle excitation from the first light source are contaminants. This example or another example may further provide wherein the contaminants are excessive adhesive material on the electronic circuit in regions of the circuit other than where the electrically conductive element is bonded to the substrate. This example or another example may further provide wherein the contaminant adhesive material is an epoxy resin. This example or another example may further provide wherein the epoxy resin includes an organic component that effectuates the fluorescent feedback second wavelength. This example or another example may further provide wherein the first light source is a blue light source and the first wavelength is in a range from about 400 nm to about 500 nm. This example or another example may further provide wherein the first wavelength of the blue light source is in a range from about 450 nm to about 475 nm; and wherein the fluorescent feedback second wavelength is greater than 500 nm. This example or another example may further provide wherein fluorescent feedback second wavelength is generated from excitation of the adhesive material contaminating the electrically conductive element or wiring, wherein the second wavelength is greater than 500 nm. This example or another example may further provide a removable connection between the filter and the viewing device so as to allow other filters having different selected filter wavelengths to be utilized in conjunction with the viewing device. This example or another example may further provide wherein the viewing device is one of a microscope and a stereoscope.

In one example, an aspect of the present disclosure may provide a method for detecting contaminant on an electronic circuit comprising: providing an electronic circuit including an electrically conductive element bonded to a substrate; emitting a light having a first wavelength toward the electronic circuit; effecting excitation of particles on the electronic circuit with the light having the first wavelength, wherein the particles generate a fluorescent feedback second wavelength in response to the excitation and the second wavelength is greater than the first wavelength; viewing the fluorescent feedback second wavelength through a filter having a selected filter wavelength that is greater than the first wavelength and less than the second wavelength; and determining whether contaminants are present on electrically conductive element based on viewing the fluorescent feedback second wavelength through the filter. This example or another example may further provide emitting a blue light and the first wavelength is in a range from about 400 nm to about 500 nm. This example or another example may further provide wherein the first wavelength is in a range from about 450 nm to about 475 nm, and the fluorescent feedback wavelength is greater than about 500 nm. This example or another example may further provide wherein determining whether contaminants are present on electrically conductive element based on viewing the fluorescent feedback second wavelength through the filter further comprises: determining whether the contaminants are excessive adhesive material on the electronic circuit in regions of the circuit other than where the electrically conductive element is bonded to the substrate. This example or another example may further provide wherein the contaminant adhesive material is an epoxy resin. This example or another example may further provide effectuating the fluorescent feedback second wavelength via an organic component included in the epoxy resin. This example or another example may further provide selecting the selected filter wavelength based on components present in an adhesive material used to bond the electrically conductive element to the substrate. This example or another example may further provide wherein viewing the fluorescent feedback second wavelength is accomplished by one of a microscope and a stereoscope. This example or another example may further provide attaching a light source for emitting the light having the first wavelength to the one of the microscope and the stereoscope.

In another example, the present disclosure may provide a system for detecting contaminants on an electronic circuit comprising: an electronic circuit having electrically conductive element bonded to a substrate; a viewing device; a first light source emitting light at a first wavelength towards the electronic circuit configured to excite particles on the electronic circuit; a fluorescent feedback second wavelength of the excited particles generated in response to particle excitation from the first light source, wherein the second wavelength is greater than the first wavelength; at least one non-transitory computer readable storage medium in having instructions encoded thereon that, when executed by one or more processors, result in the following operations for detecting contaminant material on the electronic circuit, the operations configured to: (a) emit light from the first light source at the first wavelength toward the electronic circuit; (b) effect the excitation of particles on the electronic circuit with the light having the first wavelength, wherein the particles generate the fluorescent feedback second wavelength in response to the excitation and the second wavelength is greater than the first wavelength; (c) view the fluorescent feedback second wavelength with the viewing device; and (d) determine whether contaminants are present on electrically conductive element or the circuit based on viewing the fluorescent feedback second wavelength.

In one particular example, using a 460 nanometers (nm) blue light source and a 515 nm long pass filter, it is possible to readily visualize cured epoxy resin contaminants and many other contaminants on gold bonded pads/wires/ribbons and other microelectronic components. In one example, a 460 nm blue light demonstrates the possibility to replace a UV fluorescing with blue light fluorescing to detect thin layers of cured epoxy resins on any microelectronic modules.

In accordance with one aspect of the present disclosure, one particular example may provide a system and method to fluoresce organic components in a microelectronic assembly or circuit. The system and method thereof excites organic molecules contaminating the microelectronic circuit with blue light in a range from about 400 nm to about 500 nm in combination with a long pass filter that is greater than the wavelength of the excitation light. The filter is configured to filter out any of the excitation light returning to the eye piece or a view finder that is below the selected filter wavelength so as to allow the viewer to only see or observe fluoresced light from the contaminants on the microelectronic assembly.

In yet another aspect, an example of the present disclosure may provide a system and method utilizing a light source coupled with a viewing device to detect contaminants on an electronic circuit board. This fluorescence microscopy apparatus can be easily integrated into a bench top stereoscope and does not require the use of expensive and destructive analytical techniques. Typically, blue light is used in conjunction with a filter to detect contamination from cured epoxy resins and many other contaminants on gold bond pads, wires, pads, or other electrically conductive elements on the electronic circuit

BRIEF DESCRIPTION OF THE SEVERAL VIEWS OF THE DRAWINGS

A sample embodiment of the present disclosure is set forth in the following description, is shown in the drawings and is particularly and distinctly pointed out and set forth in the appended claims.

Similar numbers refer to similar parts throughout the drawings.

DETAILED DESCRIPTION

The present disclosure relates to an apparatus for holding a light source coupled with a viewing device to detect a contaminant on a microelectronic circuit board.

Figure 1:
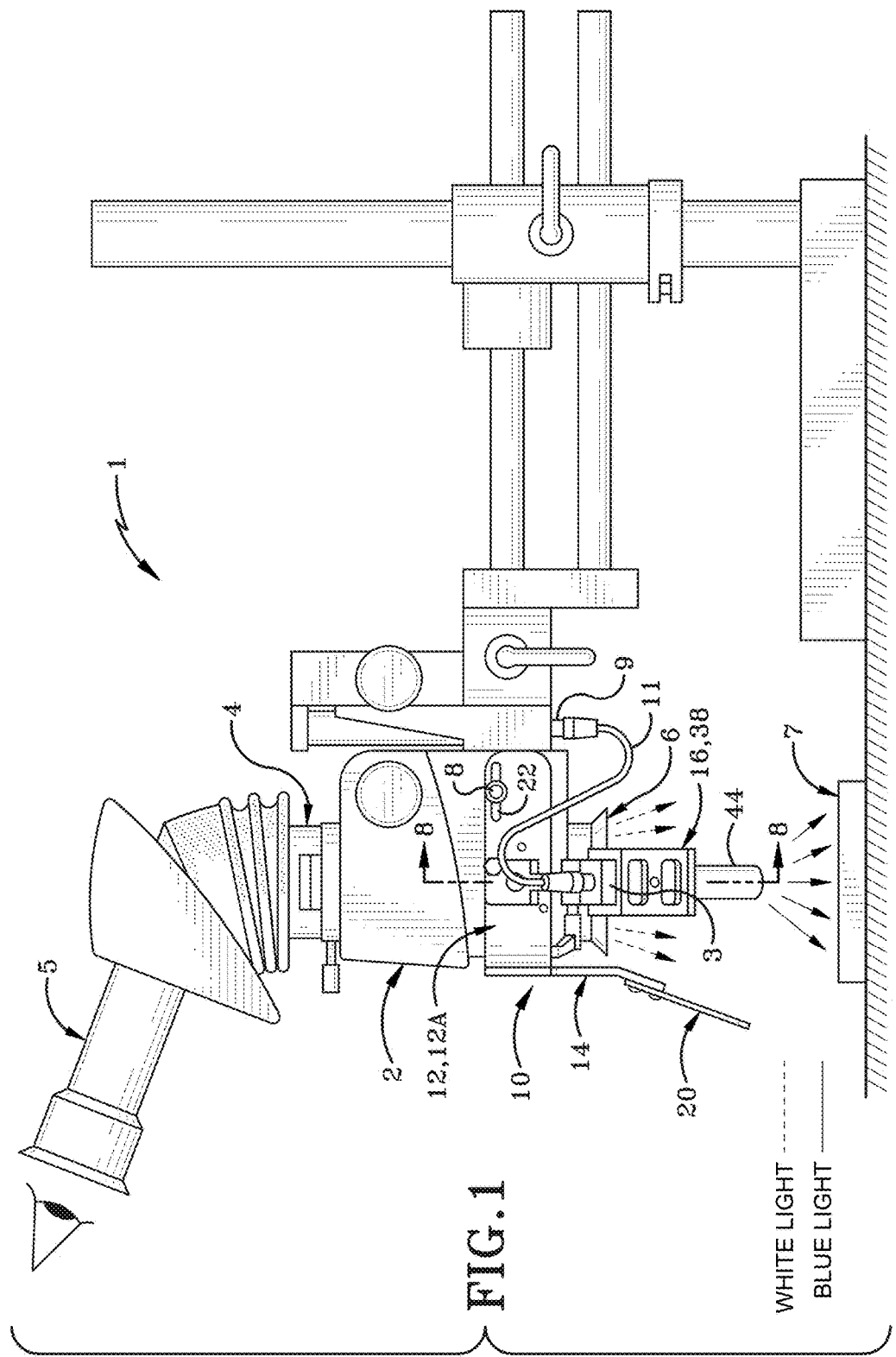
FIG. 1 is a side elevation view of a light source holding apparatus, a stereo microscope equipped with a filter, and a sample microelectronic circuit board.
Figure 2:
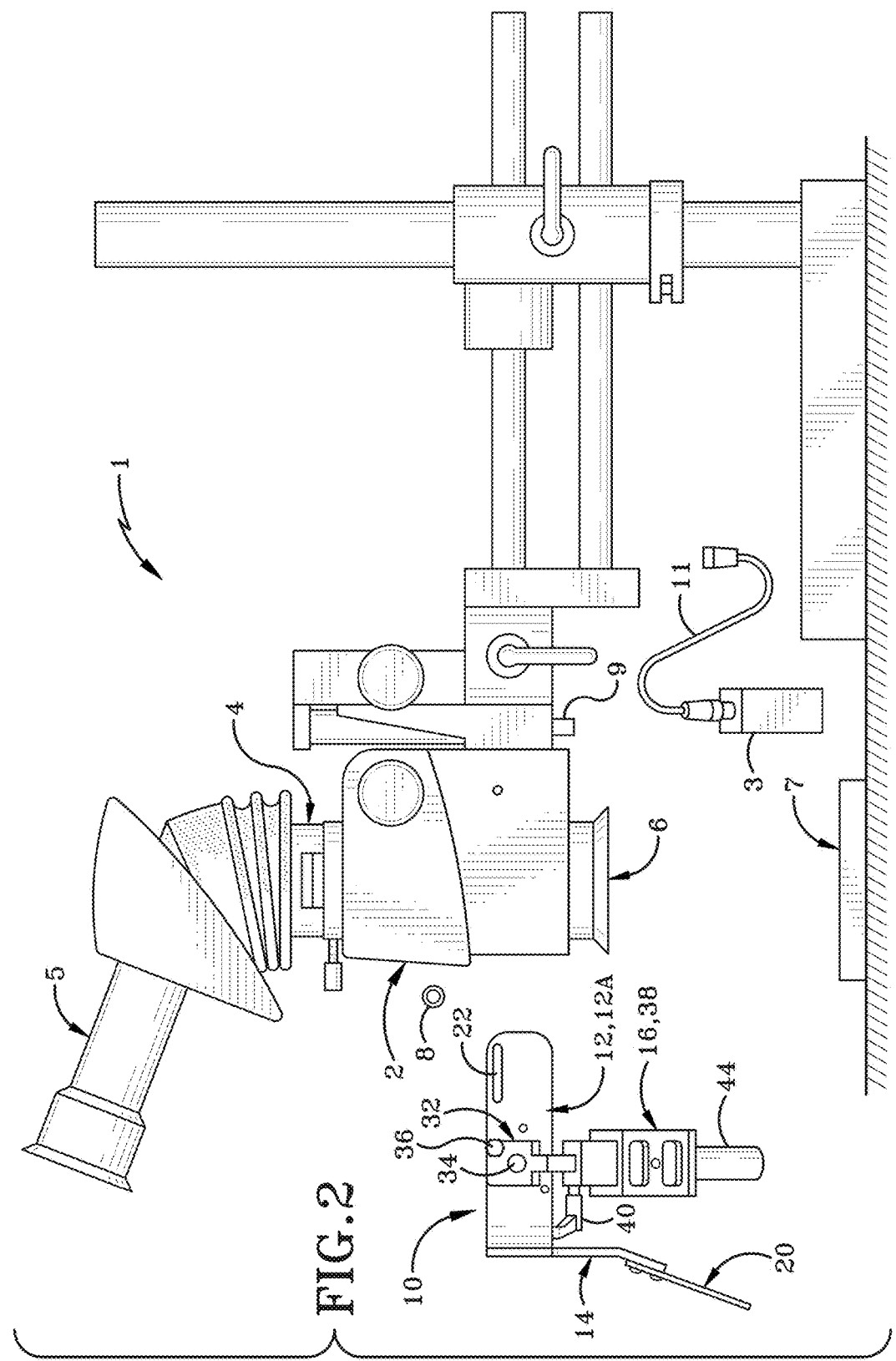
FIG. 2 is a partially exploded side elevation view of the light source holding apparatus, the stereo microscope equipped with the filter, and the sample microelectronic circuit board as in parts.

FIG. 1 and FIG. 2 depict a contaminant detection system 1 comprising a stereo microscope or other viewing device 2 equipped with a light source holding apparatus 10 and at least one blue light source 3 which has a wavelength in a range from about 400 nanometers (nm) to about 500 nm. The system 1 includes a filter 4 which is installed in a removably connected manner with the viewing device 2 between an eyepiece 5 and a white light source 6. The filter 4 is used to filter out any light which has a wavelength beyond a selected wavelength. In one example, the term "beyond" refers to filtering wavelengths shorter than the selected wavelength. A sample microelectronic circuit board 7 is placed under the blue light source 3 and white light source 6 of the microscope 2. As depicted in FIG. 2, the light source holding apparatus 10 is attached to a body of the microscope by a set of screws 8. One end of a flexible cable 11 is connected with the blue light source 3 and the other end of the flexible cable 11 is connected to a power port 9 on the viewing device 2.

In one example, viewing device 2 is a modular routine stereo microscope. One exemplary modular routine stereo microscope is manufactured by Leica Microsystems, Inc. of Buffalo Grove, Ill., model no. "M80". However, viewing device 2 may be any type of optical viewing device or optical inspection device.

As depicted in FIG. 3-FIG. 8, the light source holding apparatus 10 comprises a U-shaped main body 12, a bracket 14, a first holding member 16, a second holding member 18, and a shield 20.

The U-shaped main body 12 is a substantially rigid member configured to connect with the viewing device or microscope 2. The bracket 14 extends from a rigid connection with the main body 12. The shield 20 is connected at an opposite end of the bracket 14 from the main body 12. The U-shaped main body 12 further includes two legs, wherein the first holding member 16 is connected with the first leg and the second holding member 18 is connected with the second leg. The second holding member 18 is substantially identical in a mirrored structure and function to the first holding member 16, but is simply located on an opposing side of the main body 12.

In one exemplary embodiment, the shield 20 is an ambient light shield that is yellow in color to block the ambient light around the microscope. While shield 20 blocks ambient light, another exemplarly feature of shield 20 and its yellow pigment is a blocking filter with properties similar (but not necessarily identical) to the filter 4 installed within the microscope. This enables the operator to look through the shield and see the fluorescence of the circuit. In another embodiment, two or more shields can be attached with the light source holding apparatus 10 to block more ambient light around the microscope.

Figure 7:
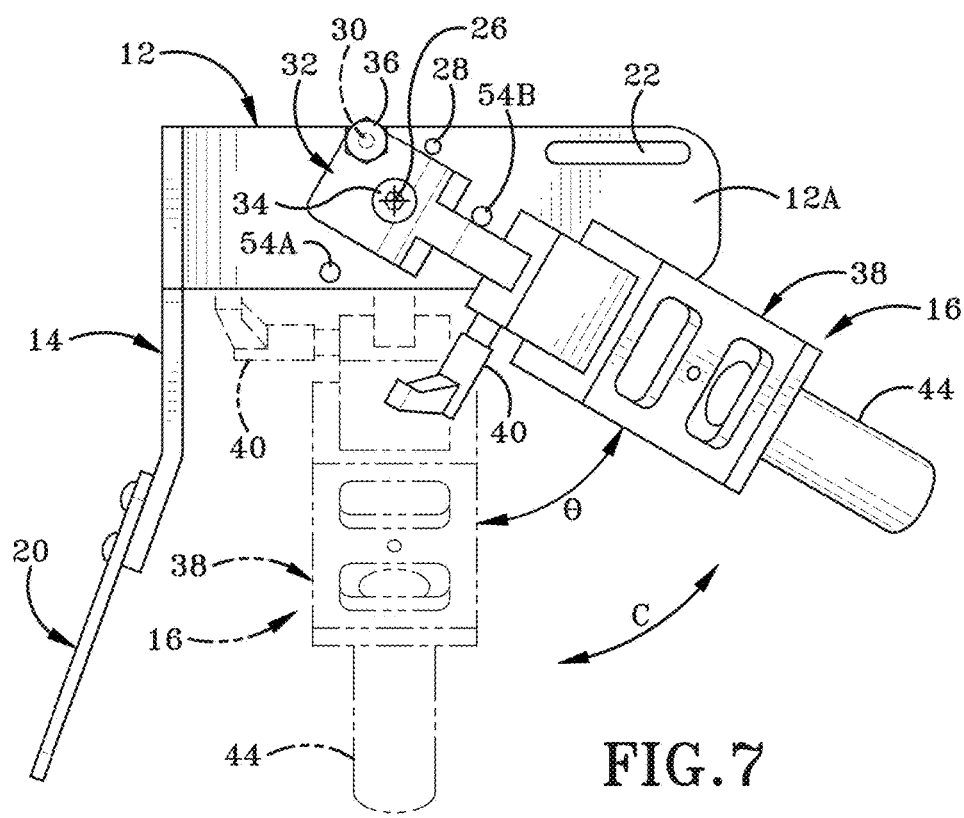
FIG. 7 is an operational side elevation view of the light source holding apparatus depicting a holding member moving from a lowered first position to a raised second position.

U-shaped main body 12 includes first leg 12A, a second leg 12B, and a central leg 12C extending between first leg 12A and second leg 12B. First leg 12A and second leg 12B extend longitudinally in the same direction substantially parallel relative to each other from rigid connections with the central leg 12C which is arranged generally transverse relative to the first leg 12A and the second leg 12B. The first leg 12A and the second leg 12B each define a transversely aligned slot 22 which is configured to receive screw 8 therethrough for attaching U-shaped main body 12 to the viewing device 2. The first leg 12A and the second leg 12B each define a first aperture 24 defining a transverse axis 26 therethrough about which the first holding member 16 and the second holding member 18 can respectively pivot. First holding member 16 and second holding member 18 pivot in a longitudinal plane about transverse axis 26. The first leg 12A and the second leg 12B further define a first hole 28 and a second hole 30. As will be described in greater detail below, first hole 28 and second hole 30 are used to secure each respective holding member 16, 18 between a lowered first position (FIG. 3) and a raised second position (FIG. 7).

Figure 3:
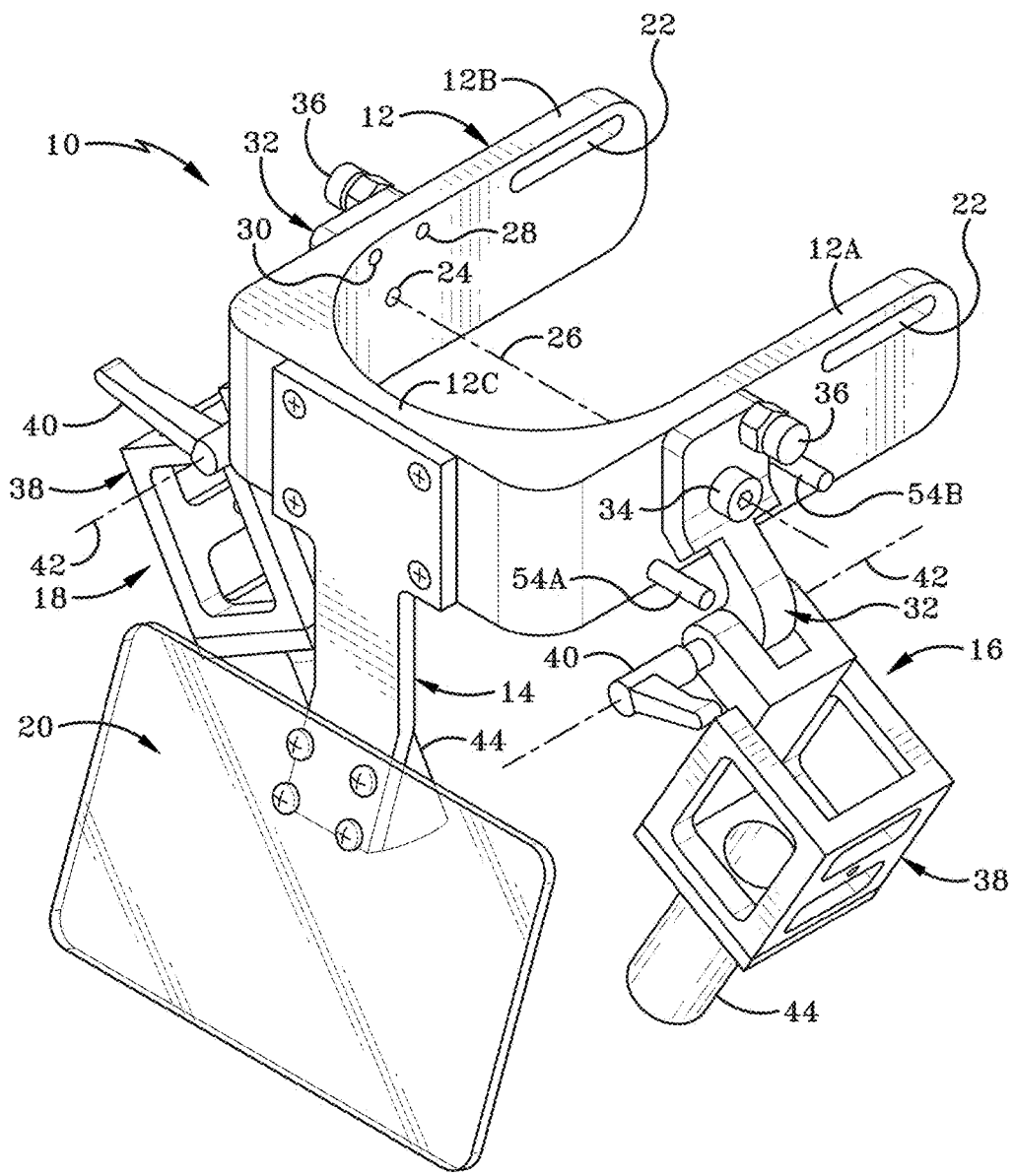
FIG. 3 is a top isometric view of the light source holding apparatus.

The first holding member 16 and the second holding member 18 are substantially mirrored about a central longitudinal axis and as such, for brevity, portions of which have been given similar reference numerals. Reference may be made with respect to the first holding member 16, however it is to be understood that a similar structure and function applies to second holding member 18. Each holding member 16, 18 includes an arm 32 that is rotatably connected to the U-shaped body 12 via a screw 34 extending through aperture 24. Screw 34 enables the arm 32 to pivot or rotate in a longitudinal plane about transverse axis 26. A spring-loaded button 36 is connected to arm 32 and may be releasably attached to extend transversely through the arm 32. When the arm 32 is in the lowered first position (as shown in FIG. 3) the button 36 is secured in first hole 28. As will be described in greater detail below, when the arm 32 of the holding member is rotated in a longitudinal direction about transverse axis 26, the button 36 disconnects from its connection with hole 28 and is inserted into second hole 30.

A lower frame 38 is connected near the lower end of the arm 32 via a pivot connection which may be securely tightened by a handle or knob 40. The handle or knob 40 is connected via a pin establishing a longitudinal axis 42 about which the lower frame 38 pivots relative to the arm 32. Accordingly, when the handle or knob 40 is loosened, the lower frame 38 may pivot in a transverse plane about the longitudinal axis 42. Thus, each holding member 16, 18 can move in a longitudinal plane about a transverse axis 26 or may move in a transverse plane about longitudinal axis 42. This movement provides functionality of illuminating the microelectronic circuit 7 with the blue light source 3 carried by the lower frame 38. Additionally, focus tubes 44 may assist in the direction of blue light downwardly towards the microelectronic circuit 7 below the viewing device 2. Additionally, the holding apparatus may translate or move up and down inasmuch as it is connected with the viewing device 2 which can move up and down as one having ordinary skill in the art would understand.

First holding member 16 and second holding member 18 may move independently relative to each other. For example, as indicated in FIG. 4-FIG. 7, the first holding member 16 may be pivoted from the lowered first position towards the raised second position (FIG. 7) by an angle θ. However, the second holding member 18 may remain in the lowered position when the first holding member 16 is in the raised position, or vice-versa. Raising either the first holding member 16 or the second holding member 18 enables an operator to access the microelectronic circuit 7 beneath the viewing device 2 in the event the holding members 16, 18 need to be lifted out of the way.

The bracket 14 is connected via a rigid connection with central leg 12C. Bracket 14 extends downwardly to enable the shield 20 to connect thereto via a set of screws, however other connections are entirely possible.

Figure 4:
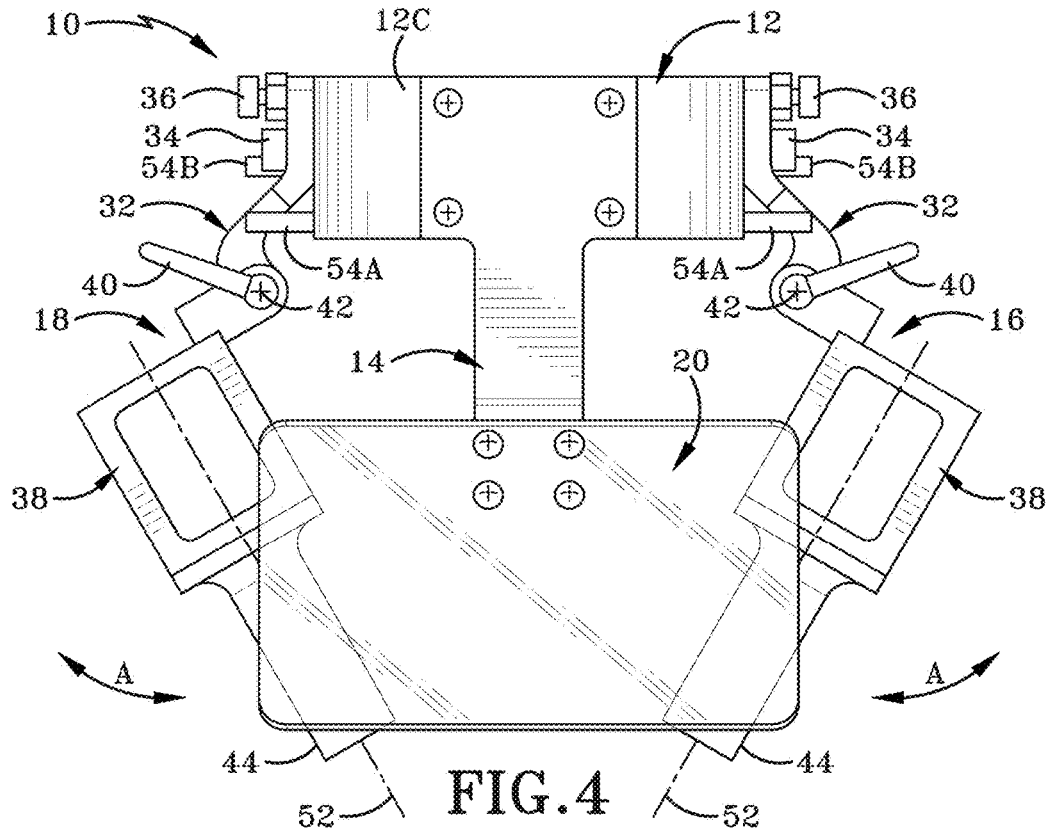
FIG. 4 is a front elevation view of the light source holding apparatus.
Figure 5:
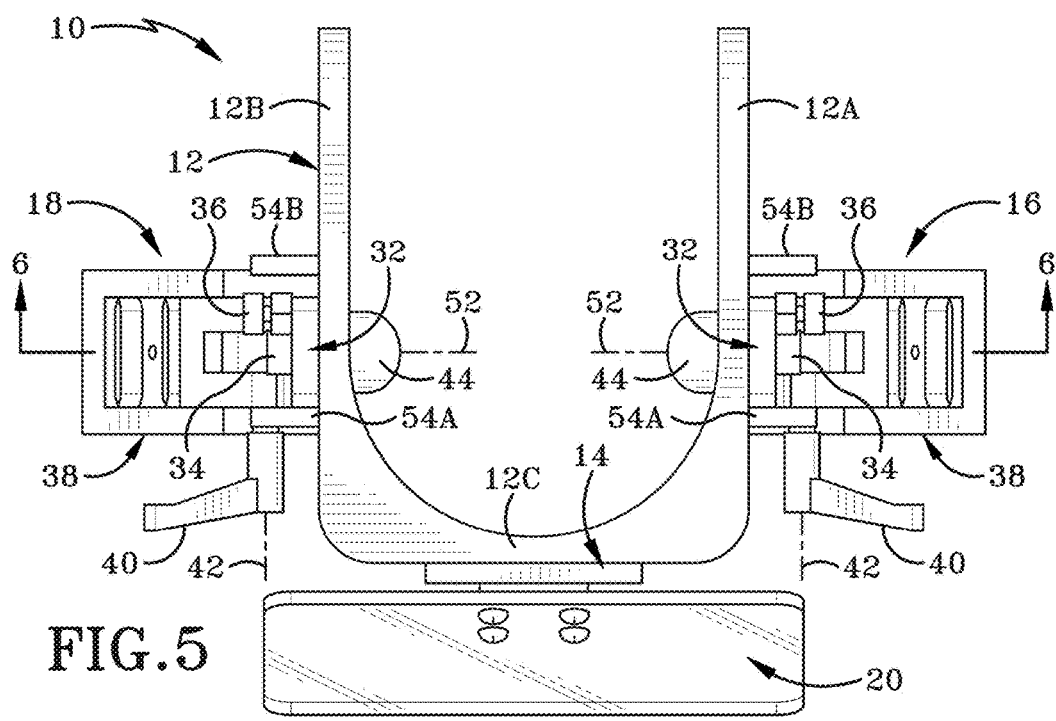
FIG. 5 is a top plan view of the light source holding apparatus.

FIG. 4 and FIG. 5 depict the operational movement of the first holding member 16 and the second holding member 18. The handles or knobs 40 may be loosened and the respective holding members 16, 18 may be pivoted in the transverse plane about longitudinal axis 42 as indicated by arrows A. The knob 40 may be loosened and the first holding member 16 may be pivoted upwardly so as to be raised and lowered depending on the size of the circuit 7 to be illuminated and the angle at which the circuit 7 is placed relative to the viewing device 2. Similarly, second holding member 18 may be pivoted about longitudinal axis 42 and may be moved in the direction of arrow A upwardly or downwardly in a pivoting manner to direct light generally in the direction of axis 52. The pivoting movement can also serve as an adjustment in order to angle the axis 52 in a different direction or region of the circuit 7 to be illuminated.

Figure 6:
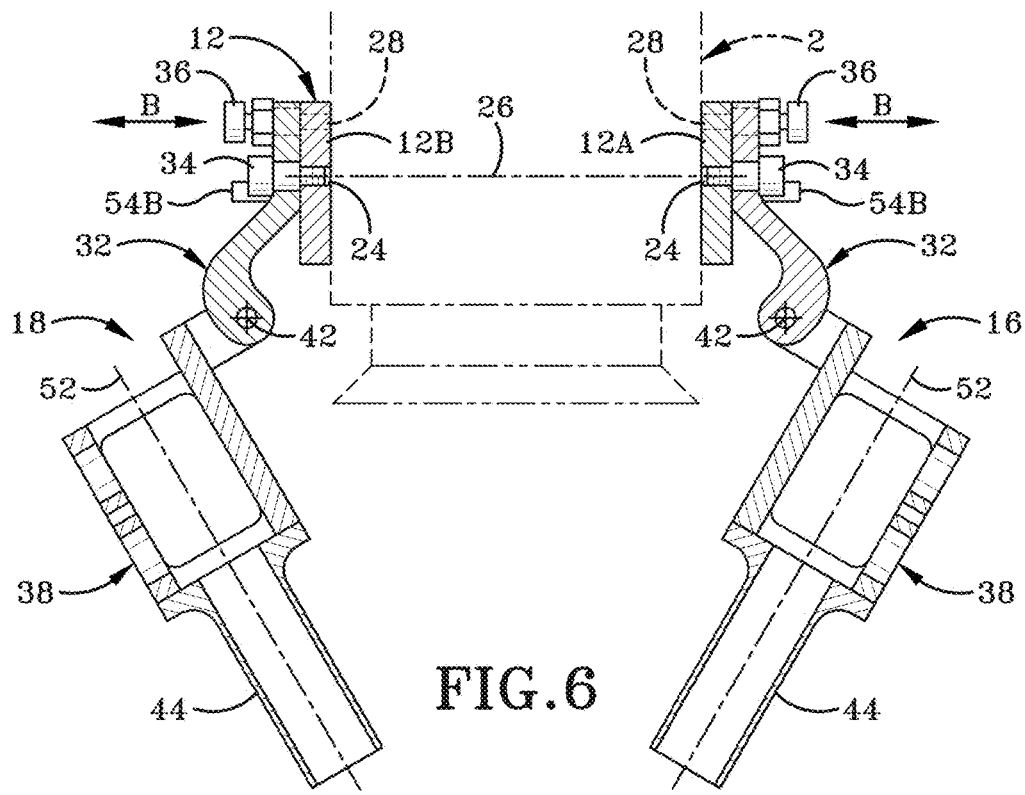
FIG. 6 is a cross section of the light source holding apparatus taken along line 6-6 of FIG. 5.

FIG. 6 and FIG. 7 depict the movement of each holding member 16, 18 in a longitudinal direction about the transverse axis 26 between the lowered first position and the raised second position. In order to effectuate movement from the lowered first position to the raised second position (FIG. 7), the button 36 may be pulled outwardly in the direction of arrow B to disengage a pin from the first hole 28. Each holding member 16, 18 may be pivoted about transverse axis 26 via pin or screw 34 and upwardly in the direction of arrow C (FIG. 7). The angle θ at which the holding member assembly rotates in the direction of arrow C is limited by at least one stop block or stop pin. In one particular example, a first stop pin 54A and a second stop pin 54B are provided on the arms of the U-shaped body 12 in order to limit the angular travel in the direction of arrow C of each respective holding member. In one embodiment, the angle θ at which each holding member pivots about transverse axis 26 is in a range from about 30° to about 90°. However, in one particular embodiment, the angle A between the lowered first position and the raised second position is about 60°.

Figure 8:
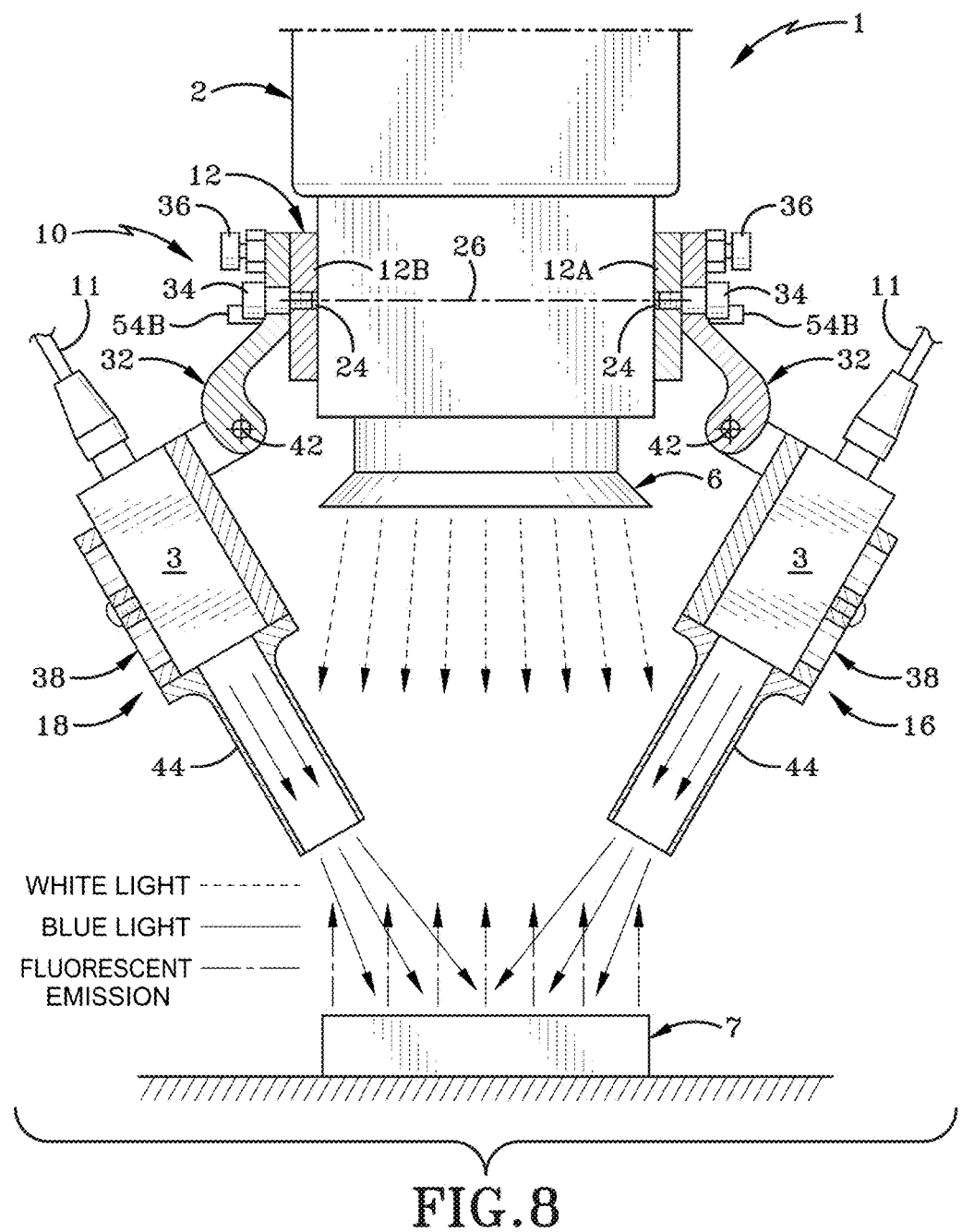
FIG. 8 is an operational cross-section of the light source holding apparatus taken along line 4-4 of FIG. 1.

As depicted in FIG. 8, when system 1 is assembled, the first holding member 16 and the second holding member 18 may each house a blue light source 3. The blue light source 3 is configured to emit blue light towards the circuit 7. The blue light is indicated in FIG. 8 by solid arrows. Further, a general white light source 6 may exist on the viewing device 2 and white light may be shined towards the circuit 7 as indicated in FIG. 8 by dashed arrows. As will be described in greater detail below, the blue light source is configured to fluoresce contaminant particles on the circuit 7. In one example, the contaminant particles are portions of epoxy resin, and more particularly, organic epoxy resin, that are excessive resin (i.e., adhesive material) on the electronic circuit in regions of the circuit other than where the electrically conductive element (i.e. wires) 50 is bonded to the circuit substrate.

The filter 4 may be housed in the viewing device 2. In one example, the filter can filter out all wavelengths less than 515 nm (i.e., the selected filter wavelength). However, in other examples, the selected filter wavelength can be altered depending on the particular purpose. Thus, it can be less than 515 nm or greater than 515 nm. The filter may be positioned anywhere in the viewer device's 2 optical light path as long as it does not prevent the blue (or indigo) light from illuminating the sample. In one example, the filter 4 is positioned between the main body of the scope and the two eyepiece tubes. In one example, it is desirable to have a band pass filter instead of a low pass filter or a high pass filter, however a high pass filter can be still used as well.

In one example, the filter 4 has a selected filter wavelength that is configured to filter out all wavelengths less than the selected filter wavelength. In one example, the selected filter wavelength is selectively set by a user to be greater than the initial excitation wavelength of the blue light. In a further example, the selected filter wavelength may also be less than the fluorescing response wavelength of the excited particulate or contaminant on the microelectronic circuit. Stated otherwise, when the excitation wavelength is a first wavelength in a blue spectrum region, and the fluorescent response wavelength is a second wavelength greater than the first wavelength, the selected filter wavelength is in between the first wavelength and the second wavelength. In one example, the blue excitation wavelength is about 465 nm, the fluorescent response feedback wavelength is about 550 nm, and the selected filter wavelength is about 515 nm. This enables filter 4 to filter out any blue light less than 515 nm viewed through the eye piece of microscope 2 but still permits the transmission of the greater wavelength fluorescent feedback second wavelength through the eye piece so as to enable the operator to detect that contaminants are present on the microelectronic circuit.

It is to be understood that different epoxies or other contaminants fluoresce at different wavelengths. Thus, the ability to interchange filters 4 with microscope 2 may be required. In such an example, filter 4 may be removably attached to the microscope 2 so as to enable filter 4 to slide or otherwise pivot out of alignment from the optical view path. In another example, a plurality of filters 4 may be formed from a glass material and can be provided to the user in a kit format depending on the desired selected filter wavelength. For example, the user may have a single stereo microscope 2 and a kit of a plurality of filters wherein each filter has a different selected wavelength. For example, a first filter 4 may include a selected filter wavelength of 400 nm. A second filter 4 may have a selected filter wavelength of 450 nm. A third filter 4 may have a selected filter wavelength of 500 nm, and so on. The functionality of the kit provided with a plurality of filters 4 would enable the user to detect a variety of contaminants depending on the fluorescent feedback wavelength. Recall, the fluorescent feedback has a wavelength greater than the initial excitation wavelength and the selected filter wavelength is intermediate (i.e., between) the first excitation wavelength and the second fluorescent response wavelength.

The following tables relate to the resultant fluorescent intensity of different epoxy resins (i.e., contaminants) that may be found on a microelectronic circuit as indicated in further detail below with respect to FIG. 9 and FIG. 10. Table 1 depicts the results of various excitation wavelengths (the first wavelength) and the resultant fluorescent intensity observed in a return fluorescent feedback wavelength of about 550 nm for Ablebond Epoxy. As indicated in Table 1 below, the greatest resultant fluorescent intensity for an Ablebond 8175 Epoxy resin contaminant on the microelectronic circuit is seen when the initial excitation emission first wavelength is about 475 nm or about 500 nm. In this instance, the filter 4 used in microscope 2 to view the fluorescent return second wavelength of about 550 nm should be in between the first wavelength and the second wavelength (i.e., the selected filter wavelength should be greater than 500 nm and less than 550 nm, such as 515 nm).

TABLE 1

Excitation wavelength and resultant fluorescent intensity of Ablebond 8175 epoxy resin at a fluorescent return wavelength of about 550 nm

| Excitation Emission (nm) | Resultant fluorescent intensity |
|---|---|
| 350 | 50,000 |
| 375 | 200,000 |
| 400 | 300,000 |
| 425 | 500,000 |
| 450 | 750,000 |
| 475 | 1,000,000 |
| 500 | 1,000,000 |

Table 2 similarly reflects the excitation emission and resultant fluorescent intensity for a different type of epoxy resin contaminant, namely, Ablebond/Henkel 84-3 "Blue Glue." The greatest resultant fluorescent intensity of the Ablebond/Henkel 84-3 "Blue Glue" occurs within an excitation emission first wavelength of about 450 nm. Thus, since the known resultant fluorescent return second wavelength is about 513 nm, the filter 4 in this scenario would need to be between the excitation emission first wavelength of 450 nm and the fluorescent return second wavelength of about 513 nm. Thus, the filter 4 in this example would be greater than 450 nm but less than 513 nm.

TABLE 2

Excitation wavelength and resultant fluorescent intensity of Ablebond/Henkel 84-3 "Blue Glue" epoxy resin at a fluorescent return wavelength of about 513 nm

| Excitation Emission (nm) | Resultant fluorescent intensity |
|---|---|
| 350 | 25,000 |
| 375 | 75,000 |
| 400 | 125,000 |
| 425 | 200,000 |
| 450 | 250,000 |

Each of the aforementioned examples and respective tables indicate that the present disclosure may be expanded to a variety of different wavelengths so long as the selected filter wavelength is greater than the excitation emission first wavelength and less than the fluorescent return second wavelength.

Figure 9:
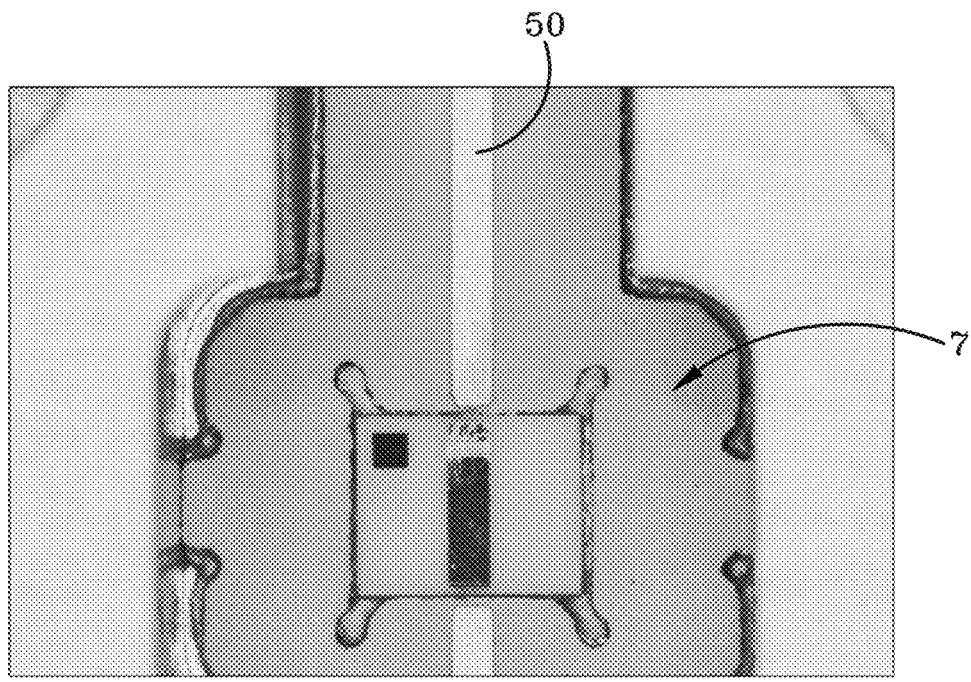
FIG. 9 is a grayscale image taken by the microscope when a blue light is off and a white light is turned on to illuminate a circuit.
Figure 10:
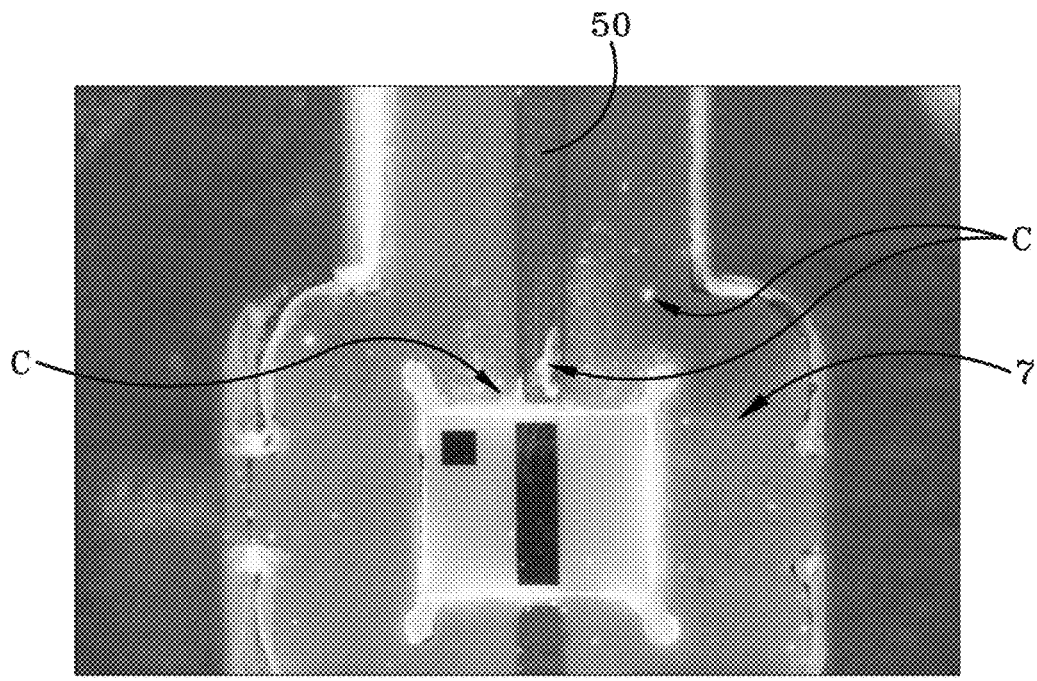
FIG. 10 is a grayscale image taken by the microscope when the blue light is on and viewing the circuit through the filter so that the fluorescence emission is made visible

FIG. 9 and FIG. 10 illustrate the result of using this particular system for detecting an organic epoxy resin formed on a microelectronic circuit board 7. FIG. 9 is an image taken only by illuminating a white light on the circuit board 7. As shown in FIG. 9, the figure shows no human visible sign of an epoxy resin on the circuit board. On the contrary, FIG. 10, which utilizes a blue light of wavelength near 460 nm combined with a Chroma glass filter 4 which can filter out wavelengths less than 515 nm, clearly shows contamination C of epoxy resin particles on the circuit board 7 and on the gold wiring 50.

Figure 11:
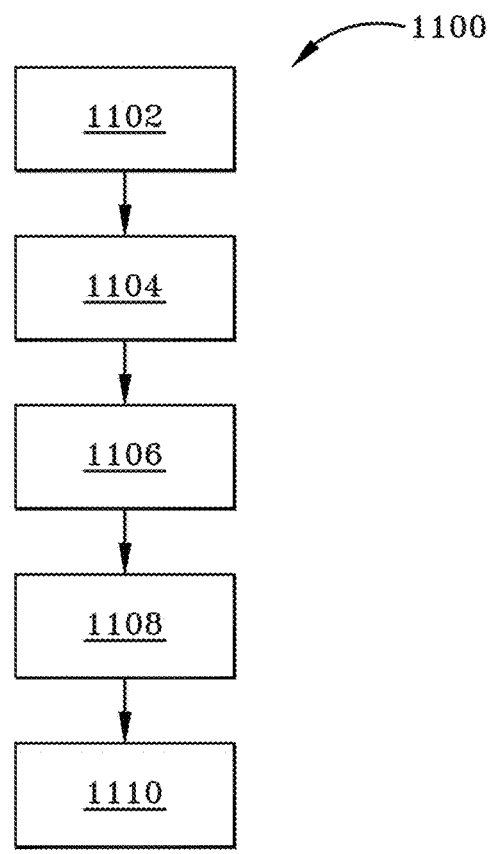
FIG. 11 is an exemplary flow chart for a method of detecting an epoxy resin on a microelectronic circuit board associated with the present disclosure.

FIG. 11 depicts an exemplary flow chart of a method 1100 for detecting contaminant (i.e., contaminant C) on an electronic circuit 7. The method 1100 may include providing an electronic circuit including an electrically conductive element 50 bonded to a substrate, which is shown generally at 1102. The method 1100 may also include emitting a light having a first wavelength toward the electronic circuit, which is shown generally at 1104. The method 1100 may also include effecting excitation of particles on the electronic circuit with the light having the first wavelength, wherein the particles generate a fluorescent feedback second wavelength in response to the excitation and the second wavelength is greater than the first wavelength, which is shown generally at 1106. The method 1100 may also include viewing the fluorescent feedback second wavelength through a filter 4 having a selected filter wavelength that is greater than the first wavelength and less than the second wavelength, which is shown generally at 1108. The method 1100 may also include determining whether contaminants are present on electrically conductive element based on viewing the fluorescent feedback second wavelength through the filter and one of (i) throwing away the electronic circuit and (ii) repairing the electronic circuit in response to the determination of whether the contaminant is present, which is shown generally at 1110. Stated otherwise, if the system determines that contaminants C are present, then the manufacturer may throw away circuit 7 or may elect to clean (i.e., repair) circuit 7.

The method 1100 of detecting contaminant from organic epoxy present on the circuit 7 may also include emitting blue light from the blue light source 3 and the first wavelength is in a range from about 400 nm to about 500 nm. In this scenario, the blue light source may be powered from the viewing device 2 or an external power source. In a more particular example, the first wavelength may be in a range from about 450 nm to about 475 nm, and the fluorescent feedback wavelength may be greater than about 500 nm.

The method 1100 of detecting contaminant from organic epoxy present on the circuit 7 may also include determining whether the contaminants are excessive adhesive material on the electronic circuit in regions of the circuit other than where the electrically conductive element is bonded to the substrate. This occurs during the manufacturing process of circuit 7 when the electrically conductive elements 50 (i.e., wires or ribbons, which are often gold) are bonded to the circuit substrate. Sometimes the adhesive material (i.e., the organic epoxy) can bleed out from the bonding region and deposit in other undesired locations which contaminate the circuit 7 and reduce its efficiency for conducting electrical signals. System 1 effectuates the fluorescent feedback second wavelength via one or more organic component(s) included in the epoxy resin.

The method 1100 of detecting contaminants on the electronic circuit may also include selecting the selected filter wavelength based on components present in an adhesive material used to bond the electrically conductive element to the substrate. As presented above in Table 1 and Table 2, the type of bonding material or epoxy used to construct the circuit is typically known in advance. Further, each epoxy fluoresces at different feedback wavelength based on the different organic components/make-up of the epoxy. Thus, since the known fluorescent feedback wavelength is known, a filter is selected that is less than the fluorescent feedback second wavelength but greater than the blue light first wavelength.

In one exemplary operation, an operator attaches a light source for emitting the light having the first wavelength to the one of the microscope and the stereoscope. This could be accomplished by installing the light source holding apparatus 10 on a microscope or stereoscope or other viewing device 2. Then, the operator provides or places a microelectronic circuitry board under the microscope. Second, the operator installs at least one blue light source into a holding member of the apparatus 10. The blue light source must be aligned with the cylinders of the light guiding tubes 44 so that the tubes can properly deliver the blue light beam to the microelectronic circuitry board. Thirdly, the blue light source 3 is turned on, and the light guiding tubes 44 are adjusted so that the blue light source can focus on the desired area on the circuit board. The operator then turns on the white light on the microscope and aligns the microelectronic board with the white light of the microscope. The filter 4 is installed in the viewing device 2 to wipe out (i.e., filter) all the unnecessary wavelengths less than the selected filter wavelength. As long as the filter is aligned with the viewer's optical light path, it can be installed anywhere in the viewing device.

In one example, a method of detecting an epoxy resin on a microelectronic circuit board 7 may include providing a circuit board which is contaminated with an epoxy resin and viewed under a microscope. Then, a light is emitted with a wavelength near a blue color. The blue color light is pointed towards a desired spot of the microelectronic circuit board. A filter which is placed in the microscope is provided to filter out any light which has a wavelength less than a selected filter wavelength. Resultant fluoresced light from the microelectronic circuit board is received through the filtering process so that the operator can detect an epoxy resin on the microelectronic circuit board.

Figure 12:
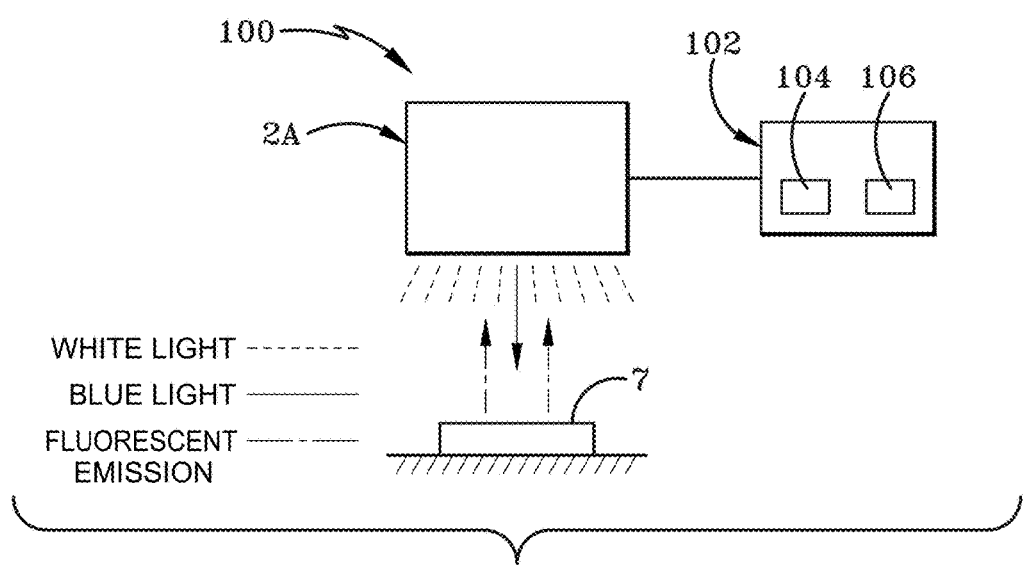
FIG. 12 is a schematic view of a computer implemented contaminant detection system.

As depicted in FIG. 12, another exemplary system of the present disclosure could be implemented through a computer implemented contaminant detection system 100 that would not require a human eye to detect the contaminant. Rather, a computer 102 having a non-transitory computer readable storage medium 104 with instructions encoded thereon for execution in one or more processors 106 could detect the contaminants C on circuit 7. The computer implemented contaminant detection system 100 would rely on automated optical inspection technology integrated with logic functions configured to detect the contaminants C on microelectronic circuit 7. Furthermore, as used herein, the computer implemented contaminant detection system 100 may also be referred to as an automated optical inspection system. The optical component provided below may be generally referred to as a viewing device 2A. As one having ordinary skill in the art would understand, a general viewing device 2A could be the automated optical inspection system.

In this example, the computer implemented contaminant detection system 100 for detecting contaminants on an electronic circuit may include: an electronic circuit 7 having electrically conductive element 50 bonded to a substrate; a viewing device 2A; a first light source 3 emitting light at a first wavelength towards the electronic circuit configured to excite particles on the electronic circuit 7; a fluorescent feedback second wavelength of the excited particles generated in response to particle excitation from the first light source, wherein the second wavelength is greater than the first wavelength; at least one non-transitory computer readable storage medium 104 in having instructions encoded thereon that, when executed, by one or more processors 106, result in the following operations for detecting contaminant material on the electronic circuit, the operations configured to: (a) emit light from the first light source 3 at the first wavelength toward the electronic circuit; (b) effect the excitation of particles on the electronic circuit with the light having the first wavelength, wherein the particles generate the fluorescent feedback second wavelength in response to the excitation and the second wavelength is greater than the first wavelength; (c) view the fluorescent feedback second wavelength with the viewing device; and (d) determine whether contaminants are present on electrically conductive element based on viewing the fluorescent feedback second wavelength.

This computer implemented system 100 would not necessarily need a physical filter 4 inasmuch as the computer 102 could be programmed to view the second wavelength without the physical filter. Accordingly, a filtering logic function could be programmed into the computer 102 to eliminate the need of the physical filter, however, the filtering logic function(s) could accomplish a similar result. For example, a basis filter function or algorithm can be included in the instructions on medium 104 which would filter out the blue light received by the viewing device (i.e., the automatic optical inspection system). In this instance, a blue light would emit towards the circuit 7. Then, the entire feedback would be received in the viewing device. Then, the logic functions implemented by computer process could digitally filter out all wavelengths received in the viewing device below a selected digital filter wavelength. For example, the blue light may be emitted at about 465 nm. Then, the circuit is viewed by viewing device 2. Thereafter, the logic filter functions are executed by one or more processors 106 to filter out all wavelengths from the viewing device 2A that are greater than the wavelength of the original blue light emission but less than the known resultant fluorescent second feedback of the epoxy or other contaminant. The computer 102 can use this information to determine whether the contamination is present and recommend whether to throw away/discard the circuit 7.

The power utilized to generate blue light from blue light source 3 may be varied depending on the optical inspection device 2A or viewing device 2 utilized in the system. For example, if the optical inspection device 2A (or 2) is a highly powerful viewing device, then less power may be needed to generate the light from the blue light source. Alternatively, if the optical inspection viewing device 2A is a lower power device (i.e., with less magnification), then a higher powered blue light source may be required (such as a blue laser).

One embodiment of the computer implemented detection system enables the rapid detection of contaminants C via an automated optical inspection (AOI) system when using the appropriate lighting and filters. The light filtration of the AOI is performed either with a lens and filter allowing only a specified range of wavelengths to reach a detector or via processing of a broad spectrum image to eliminate the excitation wavelength. The fluorescence intensity is accurately measured and specific wavelengths monitored to identify specific contaminants C. Within those wavelengths, the emission intensity is used to determine the thickness and/or concentration and/or location of the contaminant. Rejection criteria is determined and quantitatively monitored. The rejection criteria can be coded on the instructions stored in the non-transitory computer readable storage medium 104. In one example, the rejection criteria establishes a threshold of the emission intensity based on the system design and application. In one particular embodiment, rejection criteria intensity values of fluorescence is measured in arbitrary "counts" rather than photon counting or any other similar quantitative, tangible value. The particular instrument utilized may give a different result, as would every contaminant due to changes in fluorescence efficiency. Thus in the AOI system, the intensity which determines a reject would have to be concluded experimentally for each new situation. Also, any user would have to internally define rejection criteria as some products may be more sensitive to contamination than others. Essentially, testing of the rejection criteria intensity values would be determined empirically.

In a further embodiment, other excitation wavelengths such as violet, indigo, blue and green light are used for the excitation depending upon the specifics of the inspection. The appropriate optical filter for the excitation wavelength is used for the respective emission frequency in accordance with the Stokes shift in the response.

Further, the one or more processors 106 implementing the instructions from the non-transitory computer readable storage medium 104 may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), or any other suitable portable or fixed electronic device.

Also, the computer 102 (which may be a smartphone) may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers or smartphones may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various exemplary concepts may be embodied as a non-transitory computer readable storage medium (or multiple non-transitory computer readable storage media) (e.g., a computer memory, one or more floppy discs, compact discs, optical discs, magnetic tapes, flash memories, USB flash drives, SD cards, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the disclosure discussed above. The computer readable medium or media can be transportable, such that the program or programs stored thereon can be loaded onto one or more different computers or other processors to implement various aspects of the present disclosure as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present disclosure need not reside on a single computer or processor, but may be distributed in a modular fashion amongst a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

It is to be understood that a blue light source 3 can be an LED source or a laser source depending on the application. For example, if a broader area on a circuit substrate is required to be excited, then the LED source may be more desirable. If a small but strong light source is required, then a laser source may be more desirable.

Also, various concepts may be exemplified as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

While various examples or embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, embodiments of technology disclosed herein may be implemented using hardware, software, or a combination thereof. When implemented in software, the software code can be executed on any suitable processor or collection of processors, whether provided in a single computer or distributed among multiple computers.

All definitions, as defined and used herein, should be understood to control over dictionary definitions, definitions in documents incorporated by reference, and/or ordinary meanings of the defined terms.

"Logic", as used herein (for example "filtering logic"), includes but is not limited to hardware, firmware, software and/or combinations of each to perform a function(s) or an action(s), and/or to cause a function or action from another logic, method, and/or system. For example, based on a desired application or needs, logic may include a software controlled microprocessor, discrete logic like a processor (e.g., microprocessor), an application specific integrated circuit (ASIC), a programmed logic device, a memory device containing instructions, an electric device having a memory, or the like. Logic may include one or more gates, combinations of gates, or other circuit components. Logic may also be fully embodied as software. Where multiple logics are described, it may be possible to incorporate the multiple logics into one physical logic. Similarly, where a single logic is described, it may be possible to distribute that single logic between multiple physical logics.

Furthermore, the logic(s) presented herein for accomplishing various methods of this system may be directed towards improvements in existing computer-centric or internet-centric technology that may not have previous analog versions. The logic(s) may provide specific functionality directly related to structure that addresses and resolves some problems identified herein. The logic(s) may also provide significantly more advantages to solve these problems by providing an exemplary inventive concept as specific logic structure and concordant functionality of the method and system. Furthermore, the logic(s) may also provide specific computer implemented rules that improve on existing technological processes. The logic(s) provided herein extends beyond merely gathering data, analyzing the information, and displaying the results.

The indefinite articles "a" and "an," as used herein in the specification and in the claims, unless clearly indicated to the contrary, should be understood to mean "at least one." The phrase "and/or," as used herein in the specification and in the claims (if at all), should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment or example, to A only (optionally including elements other than B); in another embodiment or example, to B only (optionally including elements other than A); in yet another embodiment or example, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment or example, to at least one, optionally including more than one, A, with no B present (and optionally including elements other than B); in another embodiment or example, to at least one, optionally including more than one, B, with no A present (and optionally including elements other than A); in yet another embodiment or example, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures.

An embodiment is an implementation or example of the present disclosure. Reference in the specification to "an embodiment," "one embodiment," "some embodiments," "one particular embodiment," "an exemplary embodiment," or "other embodiments," or the like such as "an example," means that a particular feature, structure, or characteristic described in connection with the embodiments is included in at least some embodiments or examples, but not necessarily all embodiments or examples, of the present disclosure. The various appearances "an example," "an embodiment," "one embodiment," "some embodiments," "one particular embodiment," or "other embodiments," or the like, are not necessarily all referring to the same embodiments or examples.

If this specification states a component, feature, structure, or characteristic "may", "might", or "could" be included, that particular component, feature, structure, or characteristic is not required to be included. If the specification or claim refers to "a" or "an" element, that does not mean there is only one of the element. If the specification or claims refer to "an additional" element, that does not preclude there being more than one of the additional element.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the preferred embodiment of the disclosure are an example and the disclosure is not limited to the exact details shown or described.

What is claimed:

1. A system for detecting contaminants on an electronic circuit comprising:
    a viewing device adapted to view an electronic circuit having an electrically conductive element bonded to a substrate;
    a first light source emitting light at a first wavelength towards the electronic circuit adapted to excite particles on the electronic circuit at a fluorescent feedback second wavelength generated in response to particle excitation from the first light source, wherein the fluorescent feedback second wavelength is greater than the first wavelength, and the first light source is a blue light source; and
    a filter in operative communication with the viewing device having a selected filter wavelength configured to allow light to pass that is greater than the first wavelength;
    wherein at least some of the excited particles generated in response to particle excitation from the first light source are the contaminants on the electronic circuit;
    wherein the contaminants comprise an epoxy resin on the electronic circuit in regions of the circuit other than where the electrically conductive element is bonded to the substrate;
    wherein the epoxy resin includes an organic component that effectuates the fluorescent feedback second wavelength, and no additional fluorescing agent or additive, other than the organic component, is in the epoxy resin.

2. The system for detecting contaminants on the electronic circuit of claim 1, further comprising:
    wherein the selective filter wavelength is greater than the first wavelength and less than the fluorescent feedback second wavelength; and
    wherein the first wavelength is in a range from about 400 nm to about 500 nm.

3. The system for detecting contaminants on the electronic circuit of claim 2, wherein the first wavelength of the blue light source is in a range from about 450 nm to about 475 nm; and wherein the fluorescent feedback second wavelength is greater than 500 nm.

4. The system for detecting contaminants on the electronic circuit of claim 1, further comprising:
    wherein the fluorescent feedback second wavelength is generated from excitation of the epoxy resin contaminating the electrically conductive element, wherein the fluorescent feedback second wavelength is greater than 500 nm.

5. The system for detecting contaminants on the electronic circuit of claim 1, further comprising a removable connection between the filter and the viewing device so as to allow other filters having different selected filter wavelengths to be utilized in conjunction with the viewing device.

6. A system for detecting contaminants on an electronic circuit board comprising:
    a viewing device configured to view the electronic circuit board;
    a blue light source emitting light at a first wavelength that is configured to excite particles from the contaminants on the electronic circuit at a fluorescent feedback second wavelength generated in response to particle excitation from the blue light source, wherein the fluorescent feedback second wavelength is greater than the first wavelength;
    wherein the contaminants comprise an epoxy resin on the electronic circuit board in regions of the circuit board other than where an electrically conductive element is bonded to a substrate of the circuit board;
    wherein the epoxy resin includes an organic component that effectuates the fluorescent feedback second wavelength, and no additional fluorescing agent or additive, other than the organic component, is added to the epoxy resin;
    a filter in operative communication with the viewing device having a selected filter wavelength configured to allow light to pass that is greater than the first wavelength; and at least one non-transitory computer readable storage medium having instructions encoded thereon that, when executed by one or more processors, result in the following operations for detecting the contaminants on the electronic circuit board, the operations configured to:
  emit light from the blue light source at the first wavelength toward the electronic circuit board;
  effect the excitation of particles on the electronic circuit board with the blue light, wherein the particles generate a fluorescent feedback second wavelength in response to the excitation and the second wavelength is greater than the first wavelength;
  view the fluorescent feedback second wavelength with the viewing device; and
  determine whether the contaminants are present on electronic circuit board based on the fluorescent feedback second wavelength.

7. A method for detecting a contaminant on an electronic circuit comprising:
  providing an electronic circuit including an electrically conductive element bonded to a substrate, wherein an adhesive material bonds the electrically conductive element to the substrate and the adhesive material is an epoxy resin that includes an organic component and no additional fluorescing agent or additive is added to the epoxy resin;
  emitting a light from a blue light source having a first wavelength toward the electronic circuit;
  effecting excitation of particles from the contaminant on the electronic circuit with the blue light having the first wavelength, wherein the particles generate a fluorescent feedback second wavelength in response to the excitation and the second wavelength is greater than the first wavelength;
  viewing the fluorescent feedback second wavelength through a filter having a selected filter wavelength that is less than the fluorescent feedback second wavelength; and
  determining whether the epoxy resin is excessive as a contaminant present on the electrically conductive element based on the filtered fluorescent feedback second wavelength and one of (i) throwing away the electronic circuit and (ii) repairing the electronic circuit in response to the determination of whether the contaminant is present.

8. The method of claim 7, wherein the first wavelength is in a range from about 350 nm to about 500 nm.

9. The method of claim 8, wherein the first wavelength is in a range from about 450 nm to about 475 nm, and the fluorescent feedback second wavelength is greater than about 500 nm.

10. The method of claim 7, wherein determining whether the contaminant is present on electrically conductive element based on viewing the fluorescent feedback second wavelength through the filter further comprises:
  determining whether the contaminant is excessive adhesive material on the electronic circuit in regions of the circuit other than where the electrically conductive element is bonded to the substrate.

11. The method of claim 7, further comprising:
  selecting the selected filter wavelength based on the organic components present in the epoxy resin used to bond the electrically conductive element to the substrate.

12. The system for detecting contaminants according to claim 6, wherein to determine whether the contaminants are present involves comparing an emission intensity to rejection criteria.

13. The system for detecting contaminants according to claim 12, further comprising:
  arbitrary counts for use with the rejection criteria, wherein values of the emission intensity is measured with the rejection criteria in the arbitrary counts.

14. The system for detecting contaminants according to claim 6, wherein the operations are further configured to determine a location of the contaminants.

15. The system for detecting contaminants according to claim 1, further comprising a detector to detect emission intensity of the fluorescent feedback second wavelength, wherein the emission intensity is used to determine a thickness or concentration of the contaminants.

16. The system for detecting contaminants according to claim 1, further comprising a white light source for the viewing device.

* * * * *